United States Patent [19]

Currie et al.

[11] Patent Number: 5,674,894
[45] Date of Patent: Oct. 7, 1997

[54] AMIDINE DERIVATIVES USEFUL AS PLATELET AGGREGATION INHIBITORS AND VASODILATORS

[75] Inventors: Mark G. Currie, St. Charles; Foe S. Tjoeng, Manchester, both of Mo.; Mark E. Zupec, O'Fallon, Ill.

[73] Assignee: G.D. Searle & Co., Chicago, Ill.

[21] Appl. No.: 440,804

[22] Filed: May 15, 1995

[51] Int. Cl.$^6$ .............. C07D 493/04; C07D 207/12; C07D 233/02; A61K 31/34

[52] U.S. Cl. .............. 514/470; 514/422; 514/392; 514/321; 514/274; 514/424; 514/327; 514/509; 514/506; 549/464; 549/21; 549/19; 549/449; 549/414; 549/378; 548/550; 548/526; 548/311.7; 548/324.1; 548/364.4; 548/256; 548/263.2; 548/225; 548/233; 548/182; 548/199; 548/305.1; 548/251; 548/243; 548/245; 548/213; 548/214; 548/132; 548/133; 548/127; 548/129; 548/135; 548/138; 546/197; 546/221; 546/187; 546/188; 546/210; 546/208; 546/153; 546/163; 544/316; 544/296; 544/298; 544/330; 544/322; 544/238; 544/405; 544/408; 544/364; 544/370; 544/372; 544/182; 544/219; 544/215; 544/180; 544/58.6; 544/58.7; 544/58.5; 558/482; 558/488

[58] Field of Search .............. 549/464; 514/470, 514/422, 392, 321, 274; 548/526, 311.7; 546/197, 187, 153; 544/316, 296, 405, 364, 182

[56] References Cited

U.S. PATENT DOCUMENTS

| | | | |
|---|---|---|---|
| 4,517,686 | 5/1985 | Ruoslahti et al. | 3/1 |
| 4,578,079 | 3/1986 | Ruoslahti et al. | 623/11 |
| 4,589,881 | 5/1986 | Pierschbacher et al. | 623/11 |
| 4,614,517 | 9/1986 | Ruoslahti et al. | 623/11 |
| 4,661,111 | 4/1987 | Ruoslahti et al. | 623/11 |
| 4,683,291 | 7/1987 | Zimmerman et al. | 530/324 |
| 4,857,508 | 8/1989 | Adams et al. | 514/18 |
| 5,220,050 | 6/1993 | Bovy et al. | 514/357 |
| 5,239,113 | 8/1993 | Bovy et al. | 562/440 |
| 5,254,573 | 10/1993 | Bovy et al. | 514/357 |
| 5,272,162 | 12/1993 | Tjoeng et al. | 514/344 |
| 5,314,902 | 5/1994 | Tjoeng et al. | 514/357 |
| 5,344,837 | 9/1994 | Tjoeng et al. | 514/344 |
| 5,344,957 | 9/1994 | Bovy et al. | |
| 5,354,738 | 10/1994 | Tjoeng et al. | 514/19 |
| 5,378,727 | 1/1995 | Bovy et al. | 514/465 |

FOREIGN PATENT DOCUMENTS

| | | |
|---|---|---|
| 381033 | 8/1990 | European Pat. Off. . |
| 445796 | 11/1991 | European Pat. Off. . |
| 503348 | 2/1992 | European Pat. Off. . |
| 512831 | 11/1992 | European Pat. Off. . |
| 539343A1 | 4/1993 | European Pat. Off. . |
| WO9403421-A2 | 2/1994 | WIPO . |

OTHER PUBLICATIONS

Grant & Hackh's Chemical Dictionary, 5th Ed., McGraw-Hill, (1987) p. 394.
Moncada, S. et al. Biochem. Pharm. 38, 1709–1715 (1989).
Wessberg et al. Europ. J. Pharmacol. 106, 59–67 (1985).
Alspaugh, J.A. et al. Infection and Immunity 59, 2291–2296 (1991).
Wallace, J.L. et al. Europ. Jour. Pharm., 257, 249–255 (1994).
MacIntyre, I. et al. Proc. Natl. Acad. Sci. USA, 88 2936–2940 (1991).
Kozcewiak, M. et al. Biochem. 23, 1767–1774 (1984).
Plow, E.F. et al., Proc. Natl. Acad. Sci. 82, 8057–8061 (1985).
Ruggeri, Z.R. et al. Proc. Natl. Acad. Sci. 83, 5708–5712 (1986).
Ginsberg, M. et al. J. Biol. Chem. 260 (7) 3931–3936 (1985).
Haverstick, D.M. et al. Blood 66 (4), 946–952 (1985).
Ruoslati, E. et al. Science 238, 491–497 (1987).

*Primary Examiner*—Mukund J. Shah
*Assistant Examiner*—King Lit Wong
*Attorney, Agent, or Firm*—D. A. Bennett

[57] ABSTRACT

The current invention discloses novel amidine derivatives with nitric oxide donating property that can inhibit platelet aggregation and promote vasodilation in a single compound.

7 Claims, No Drawings

AMIDINE DERIVATIVES USEFUL AS PLATELET AGGREGATION INHIBITORS AND VASODILATORS

BACKGROUND OF THE INVENTION

1. Field of the Invention

The present invention relates to novel amidine derivatives with nitric oxide donating property, pharmaceutical compositions or preparations thereof, and to their use in therapy, in particular their use as inhibitors of platelet aggregation, platelet adhesion and restenosis, anti-atherogenic agent, and vasodilator for treatment of unstable angina, stroke, myocardial infarction, myocardial ischemia and reperfusion, splanchnic ischemia and reperfusion, atherosclerosis, congestive heart failure, ischemic arrhrythmia, thrombosis, hypertension, pulmonary disease, metastasis and osteoporosis.

2. Related Art

Fibrinogen is a glycoprotein present as a normal component of blood plasma. It participates in platelet aggregation and fibrin formation in the blood clotting mechanism.

Platelets are cellular elements found in whole blood which also participate in blood coagulation. Fibrinogen binding to platelets is important to normal platelet function in the blood coagulation mechanism. When a blood vessel receives an injury, the platelets binding to fibrinogen will initiate aggregation and form a thrombus. Interaction of fibrinogen with platelets occurs through a membrane glycoprotein complex, known as GP IIb/IIIa; this is an important feature of the platelet function. Inhibitors of this interaction are useful in modulating platelet thrombus formation.

It is also known that another large glycoprotein named fibronectin, which is a major extracellular matrix protein, interacts with platelets. Various relatively large polypeptide fragments in the cell-binding domain of fibronectin have been found to have cell-attachment activity. See U.S. Pat. Nos. 4,517,686; 4,589,881; and 4,661,111. Certain relatively short peptide fragments from the same molecule were found to promote cell attachment to a substrate when immobilized on the substrate or to inhibit attachment when in a solubilized or suspended form. See U.S. Pat. Nos. 4,578,079 and 4,614,517.

In U.S. Pat. No. 4,683,291, inhibition of platelet function is disclosed with synthetic peptides designed to be high affinity antagonists of fibrinogen binding to platelets. U.S. Pat. No. 4,857,508 discloses tetrapeptides having utility as inhibitors of platelet aggregation.

Other synthetic peptides and their use as inhibitors of fibrinogen binding to platelets are disclosed by Kozcewiak et al., *Biochem.* 23, 1767–1774 (1984); Plow et al., *Proc. Natl. Acad. Sci.* 82, 8057–8061 (1985); Ruggeri et al., *Ibid.* 83, 5708–5712 (1986); Ginsberg et al., *J. Biol. Chem.* 260 (7), 3931–3936 (1985); Haverstick et al., *Blood* 66 (4), 946–952 (1985); and Ruoslahti and Piersbacher, *Science* 238, 491–497 (1987). Still other such inhibitory peptides are disclosed in European Patent Applications 275,748 and 298,820.

European Patent Applications 512,831 discloses piperidinylalkyl-azacycloalkanones which inhibit the binding of fibrinogen to blood platelets and therefore are useful for inhibiting the aggregation of blood platelets. European Patent Applications 503,548 discloses cyclic urea derivatives (imidazolones and triazolones) useful in inhibiting cellular interactions thereby useful for treating or preventing thrombosis, embolisms and metastases. European Patent Application 496,378 discloses amidinobiphenyl compounds which inhibit cell cell and cell-matrix interaction and are thus useful for treating thrombosis, cerebro vascular diseases, pulmonary embolisms, myocardial infarction, arterioscleroisis, osteoporosis and tumor metastases.

European Patent Application 445,796 discloses acetic acid derivatives which have inhibitory action on the binding of adhesive proteins to blood platelets as well as on blood platelet aggregation and cell cell adhesion. European Patent Application 372,486 discloses N-acyl β-amino acid derivatives and their salts. The disclosed compounds are useful for inhibiting platelet aggregation in the treatment of thrombosis, stroke, myocardial infarction, inflammation and arteriosclerosis, and for inhibiting metastasis. European Patent Applications 381,033 discloses amidino or guanidinoaryl substituted alkanoic acid derivatives useful for the treatment of thrombosis, apoplexy, cardiac infarction, inflammation, arteriosclerosis and tumors.

International Applications WO 95/06038 and WO 94/22820 disclose phenylamidine derivatives useful as platelet aggregation inhibitors. U.S. Pat. Nos. 5,220,050, 5,239,113, 5,254,573, 5,272,162, 5,378,727, 5,314,902, 5,344,957, 5,344,837 and 5,354,738 disclose novel platelet aggregation inhibitors.

It has been known since the early 1980's that the vascular relaxation brought about by acetylcholine is dependent on the presence of the endothelium and this activity was ascribed to a labile humoral factor termed endothelium-derived relaxing factor (EDRF). The activity of nitric oxide (NO) as a vasodilator has been known for well over 100 years and NO is the active component of amylnitrite, glyceryltrinitrate and other nitrovasodilators. The recent identification of EDRF as NO has coincided with the discovery of a biochemical pathway by which NO is synthesized from the amino acid L-arginine by the enzyme NO synthase. The NO released by the constitutive enzyme acts as a transduction mechanism underlying several physiological responses. The NO produced by the inducible enzyme is a cytotoxic molecule for tumor cells and invading microorganisms.

NO is the endogenous stimulator of the soluble guanylate cyclase and is involved in a number of biological actions in addition to endothelium-dependent relaxation including cytotoxicity of phagocytic cells and cell-to-cell communication in the central nervous system (see Moncada et al, *Biochemical Pharmacology*, 38, 1709–1715 (1989) and Moncada et al, *Pharmacoloaical Reviews*, 43, 109–142 (1991). Furthermore, NO has been shown to posses antithrombotic (see Radomski et al, *British Journal of Pharmacolgy*, 92, 639–646 (1987), Moncada et al. *Journal of Cardiovascular Pharmacology* 17, S25 (1991), Yao et al., *Circulation*, 86, 1302–1309 (1992), Byrne et al. World Patent application WO9403421-A2 and Schonafinger et al., German Patent application DE4223800-A1), bronchorelaxant (Persson et al. *European Journal of Pharmacology*, 249, R7–R8 (1993), antiinflammatory, microbialcidal (Alspaugh and Granger, *Infection and Immunity* 59, 2291–2296 (1991) and gastroprotective (see Wallace et al. *European Journal of Pharmacology*, 257, 249–255 (1994) effects in animal models. In addition, nitric oxide has been suggested to be effective against the loss of bone in in vitro models of osteoporosis (MacIntyre et al. *Proc. Natl. Acad. Sci. USA* 88, 2936–2940 (1991).

Thus, these properties make nitric oxide an ideal agent to enhance the actions of the platelet aggregation inhibitors in the treatment of various diseases mentioned earlier by both increasing their biological effects as well as by reducing their side effects. The present invention relates to novel nitrate and nitrite esters of platelet aggregation inhibitors, processes for their preparation, pharmaceutical compositions containing them, and methods for their use.

SUMMARY OF THE INVENTION

In accordance with the present invention novel amidino derivatives are provided. These novel inhibitor compounds can be represented by the following chemical formula (I):

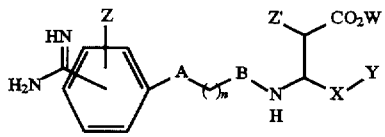

or a pharmaceutically acceptable salt thereof, wherein;

A is independently selected from the group consisting of:

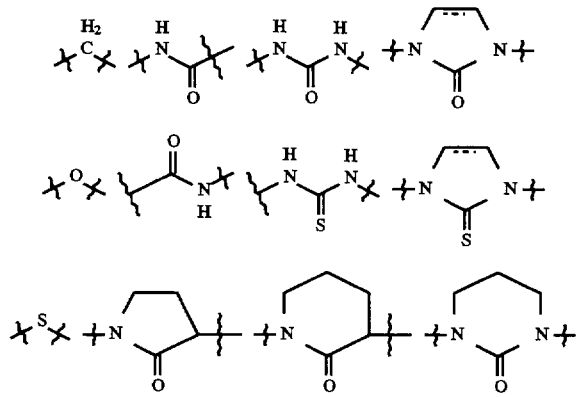

wherein the dotted line indicates a single or a double bond and

B is selected from a group consisting of carbonyl or iminocarbonyl group;

W is selected from the group consisting of hydrogen, lower alkyl radicals, lower alkenyl radicals, lower alkynyl radicals, alicyclic hydrocarbon radicals and aromatic hydrocarbon radicals, wherein all of said radicals are optionally substituted with hydroxyl, lower alkyl, lower alkoxy, halogen, nitro, amino, acyloxy, phenyl and naphthyl which may be optionally substituted with halogen, nitro, lower alkoxy, and lower alkyl;

Z, Z' are independently selected from the group consisting of hydrogen, halogen, cyano, sulfonyl, hydroxy, lower alkoxy, and lower alkyl radicals;

X is a lower alkyl radicals, lower alkenyl radicals, lower alkynyl radicals, carbonyl, alicyclic or heterocyclic radicals;

Y is a nitrate ($ONO_2$), nitrite (ONO), or nitric oxide donating compound preferably a furoxan derivative or an organic nitrate/nitrite compound such as S-nitroso-cysteine, S-nitroso-penicillamine and

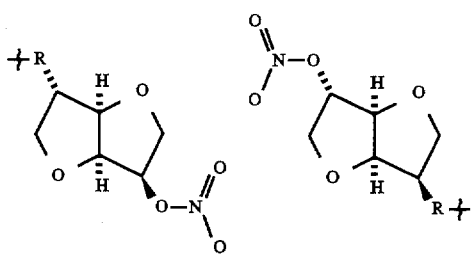

wherein R is an oxygen or an imino group;

n is an integer 1 to about 4.

The invention further relates to pharmaceutical compositions comprising a compound of Formula (I). Such compounds and compositions have usefulness as inhibitors of platelet aggregation, platelet adhesion and restenosis, anti-atherogenic agent, and vasodilator for treatment of unstable angina, stroke, myocardial infarction, myocardial ischemia and reperfusion, splanchnic ischemia and reperfusion, atherosclerosis, congestive heart failure, ischemic arrhrythmia, thrombosis, hypertension, pulmonary disease, metastasis and osteoporosis. The invention also relates to a method of inhibiting platelet aggregation and platelet adhesion, preventing restenosis, preventing atherosclerosis, and promoting vasodilation in a mammal in need of such treatment.

DETAILED DESCRIPTION OF THE INVENTION

A preferred embodiment of the present invention is a compound of the formula I;

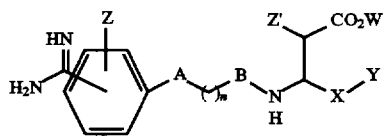

or a pharmaceutically acceptable salt thereof, wherein;

A is selected from the group consisting of

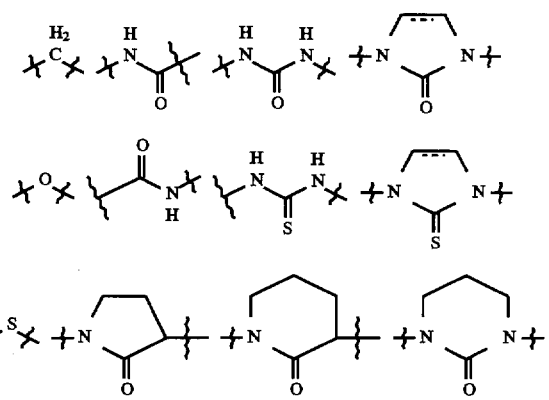

wherein the dotted line indicates a single or a double bond

B is selected from a group consisting of carbonyl or iminocarbonyl group;

W is selected from the group consisting of hydrogen, lower alkyl radicals of 1 to about 6 carbon atoms, lower alkenyl radicals of 2 to about 6 carbon atoms, alicyclic hydrocarbon radicals of 3 to about 6 carbon atoms, and aromatic hydrocarbon radicals of 6 to about 12 carbon atoms, wherein all of said radicals are optionally substituted with hydroxyl, lower alkoxy, lower alkyl, halogen, nitro, amino, and acyloxy;

Z, Z' are independently selected from the group consisting of hydrogen, halogen, cyano, sulfonyl, hydroxy, lower alkyl and lower alkoxy radicals;

X is a lower alkyl radicals, lower alkenyl radicals, lower alkynyl radicals, carbonyl, alicyclic or heterocyclic radicals;

Y is a nitrate ($ONO_2$), nitrite (ONO), or nitric oxide donating group preferably a furoxan derivative or an organic nitrate/nitrite (ONO) compound such as S-nitroso-cysteine, S-nitroso-penicillamine and

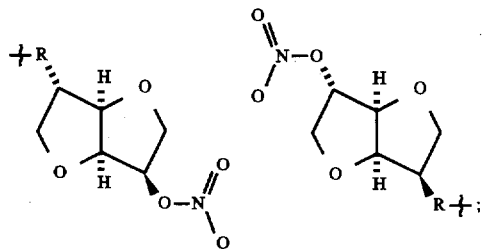

wherein R is an oxygen or an imino group;

n is an integer 1 to about 4.

Another preferred embodiment of the present invention is a compound of the formula I:

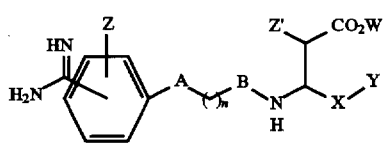

or a pharmaceutically acceptable salt thereof, wherein
A is selected from the group consisting of

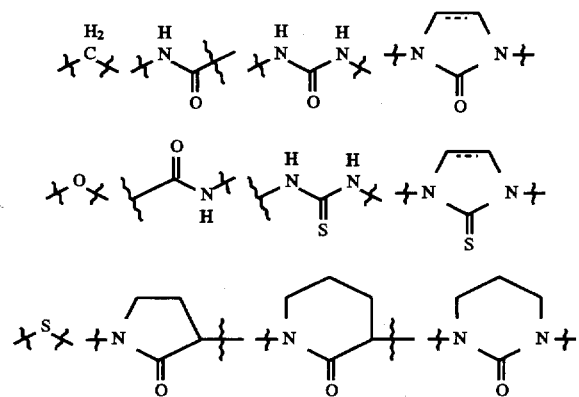

wherein the dotted line indicates a single or a double bond

B is selected from a group consisting of carbonyl or iminocarbonylradicals;

W is selected from the group consisting of hydrogen, lower alkyl radicals of 1 to about 6 carbon atoms, alicyclic hydrocarbon radicals of 3 to about 6 carbon atoms, and aromatic hydrocarbon radicals of 6 to about 12 carbon atoms, wherein all of said radicals are optionally substituted with hydroxyl, lower alkoxy, lower alkyl, halogen, nitro, amino, and acyloxy;

Z, Z' are independently selected from the group consisting of hydrogen, halogen, alkoxy,and lower alkyl radicals;

X is a lower alkyl, carbonyl or alicyclic radicals;

Y is a nitrate ($ONO_2$) or nitric oxide donating group preferably a furoxan derivative or an organic nitrate compound such as

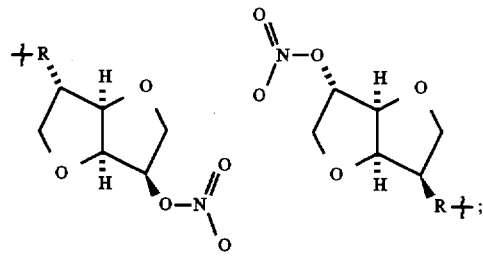

wherein R is an oxygen or an imino group;

n is an integer 1 to about 3.

Another preferred embodiment of the present invention is a compound of the formula I:

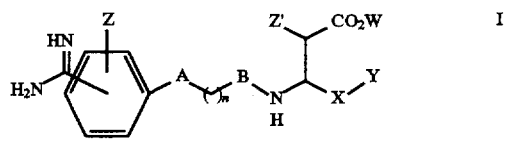

or a pharmaceutically acceptable salt thereof, wherein A is

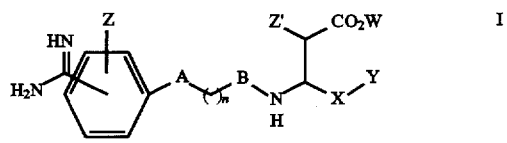

wherein the dotted line indicates a single or a double bond

B is selected from a group consisting of carbonyl or iminocarbonyl radicals;

W is selected from the group consisting of hydrogen, methyl, ethyl, propyl, cyclohexyl radicals;

Z, Z' are independently selected from the group consisting of hydrogen and hydroxy radicals;

X is a carbonyl or alicyclic radicals;

Y is a nitrate ($ONO_2$) or nitric oxide donating group preferably a furoxan derivative or an organic nitrate compound such as:

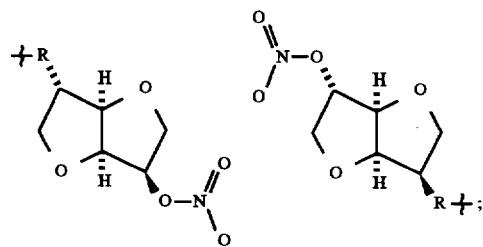

wherein R is an oxygen or an imino group;

n is an integer 1 to about 3.

Another preferred embodiment of the present invention is a compound of the formula I:

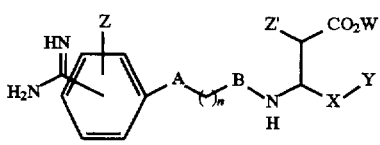

or a pharmaceutically acceptable salt thereof, wherein A is

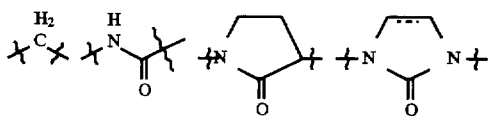

Wherein the dotted line indicates a single or a double bond and B is a carbonyl group;

W is selected from the group consisting of hydrogen, ethyl and cyclohexyl radicals;

Z, Z' are hydrogen;

X is a carbonyl radical;

Y is a nitric oxide donating group preferably an organic nitrate compound such as:

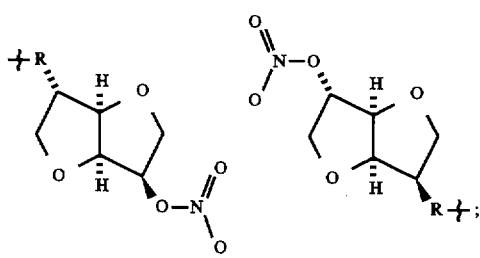

wherein R is an oxygen;

n is an integer 1 to about 2.

While it may be possible for the preparations or compounds as defined above to be administered as the raw chemical, it is preferable to present them as a pharmaceutical formulation. According to a further aspect, the present invention provides a pharmaceutical formulation comprising a preparation or a compound as defined above or a pharmaceutically acceptable salt or solvate thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof.

The formulations include those suitable for oral, parenteral (including subcutaneous, intradermal, intramuscular, intravenous and intraarticular), rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. All methods include the step of bringing into association a preparation or a compound as defined above or a pharmaceutically acceptable salt or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein.

Formulations for parenteral administration include aqueous and non-aqueous sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example, saline, water-for-injection, immediately prior to use. Extemporaneous injection solutions and suspensions may be prepared from sterile powders, granules and tablets of the kind previously described.

Formulations for rectal administration may be presented as a suppository with the usual carriers such as cocoa butter or polyethylene glycol.

Formulations for topical administration in the mouth, for example buccally or sublingually, include lozenges comprising the active ingredient in a flavored basis such as sucrose and acacia or tragacanth, and pastilles comprising the active ingredient in a basis such as gelatin and glycerin or sucrose and acacia.

Preferred unit dosage formulations are those containing an effective dose, as hereinbelow recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavoring agents.

The compounds of the invention may be administered orally or via injection at a dose of from 0.1 to 500 mg/kg per day. The dose range for adult humans is generally from 5 mg to 5g/day. Tablets or other forms of presentation provided in discrete units may conveniently contain an amount of compound of the invention which is effective at such dosage or as a multiple of the same, for instance, units containing 2.5 mg to 500 mg, usually around 5 mg to 200 mg.

The compounds of formula (I) are preferably administered orally or by injection (intravenous or subcutaneous). The precise amount of compound administered to a patient will be the responsibility of the attendant physician. However, the dose employed will depend on a number of factors, including the age and sex of the patient, the precise disorder being treated, and its severity. Also, the route of administration may vary depending on the condition and its severity.

As utilized herein, the term "lower alkyl", alone or in combination, means an acyclic alkyl radical containing from 1 to about 10, preferably from 1 to about 8 carbon atoms and more preferably 1 to about 6 carbon atoms. Examples of such radicals include methyl, ethyl, n-propyl, isopropyl, n-butyl, isobutyl, sec-butyl, tert-butyl, pentyl, isoamyl, hexyl, octyl and the like.

The term "lower alkenyl" refers to an unsaturated acyclic hydrocarbon radical in so much as it contains at least one double bond. Such radicals containing from about 2 to about 10 carbon atoms, preferably from about 2 to about 8 carbon atoms and more preferably 2 to about 6 carbon atoms. Examples of suitable alkenyl radicals include propylenyl, buten-1-yl, isobutenyl, penten-1-yl, 2-2-methylbuten-1-yl, 3-methylbuten-1-yl, hexen-1-yl, hepten-1-yl, and octen-1-yl, and the like.

The term "lower alkynyl" refers to an unsaturated acyclic hydrocarbon radicals in so much as it contains one or more triple bonds, such radicals containing about 2 to about 10 carbon atoms, preferably having from about 2 to about 8 carbon atoms and more preferably having 2 to about 6 carbon atoms. Examples of suitable alkynyl radicals include ethynyl, propynyl, butyn-1-yl, butyn-2-yl, pentyn-1-yl, pentyn-2-yl, 3-methylbutyn-1-yl, hexyn-1-yl, hexyn-2-yl, hexyn-3-yl, 3,3-dimethyl-butyn-1-yl radicals and the like.

The term "lower alkoxy", alone or in combination, means an alkyl ether radical wherein the term alkyl is as defined above and most preferably containing 1 to about 4 carbon atoms. Examples of suitable alkyl ether radicals include methoxy, ethoxy, n-propoxy, isopropoxy, n-butoxy, isobutoxy, sec-butoxy, tert-butoxy and the like.

The term "alicyclic" or "cycloalkyl" means a aliphatic radical in a ring with 3 to about 10 carbon atoms, and preferably from 3 to about 6 carbon atoms. Examples of suitable alicyclic radicals include cyclopropyl, cyclobutyl, cyclopentyl, cyclohexyl, cyclohexenyl and the like.

The term "aromatic hydrocarbon" means an aromatic radical 4 to about 16 carbon atoms, preferably 6 to about 12 carbon atoms, more preferably 6 to about 10 carbon atoms. Examples of suitable aromatic hydrocarbon radicals include phenyl, naphthyl, and the like.

The term "heterocyclyl radical" means a saturated or unsaturated cyclic hydrocarbon radical including aromatic systems with 4 to about 10 carbon atoms, preferably about 5 to about 6; wherein 1 to about 4 carbon atoms are replaced by nitrogen, oxygen or sulfur. The "heterocyclic radical" may be fused to an aromatic hydrocarbon radical. Suitable examples include pyrrolyl, pyridinyl, pyrazolyl, triazolyl, pyrimidinyl, pyridazinyl, oxazolyl, isoxazolyl, thiazolyl, imidazolyl, indolyl, thienyl, furanyl, tetrazolyl, 2-pyrrolinyl, 3-pyrrolinyl, pyrrolindinyl, 1,3-dioxolanyl, 2-imidazonlinyl, imidazolidinyl, 2-pyrazolinyl, pyrazolidinyl, isoxazolyl, isothiazolyl, oxadiazolyl, triazolyl, thiadiazolyl, 2H-pyranyl, 4H-pyranyl, piperidinyl, 1,4-dioxanyl, morpholinyl, 1,4-dithianyl, thiomorpholinyl, pyrazinyl, piperazinyl, triazinyl, 1,3,5-trithianyl, benzo(b)thiophenyl, benzimidazolyl, quinolinyl, and the like.

The term "halogen" means fluorine, chlorine, bromine or iodine.

The term "prodrug" refers to a compound that is made more active in vivo.

As used herein, reference to "treatment" of a patient is intended to include prophylaxis.

All references, patents or applications, U.S. or foreign, cited in the application are hereby incorporated by reference as if written herein.

Starting materials used to make the present invention are commercially available such as from Sigma.

Two general synthetic schemes are outlined below for the compounds of the present invention.

SCHEME I

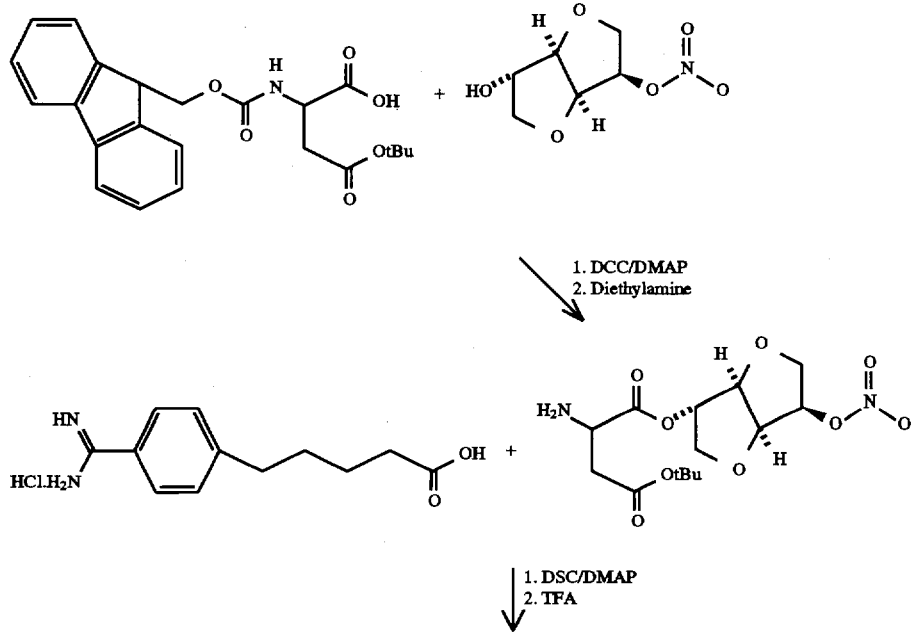

-continued
SCHEME I
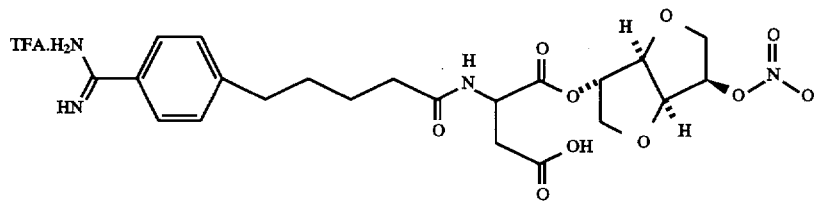
↓ HCl/ethanol
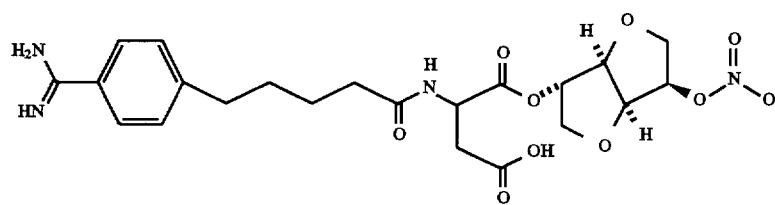
SCHEME II
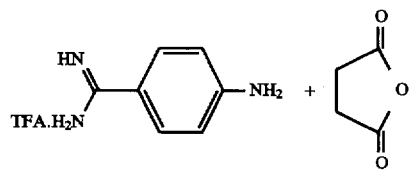
↓ DMAP/pyridine
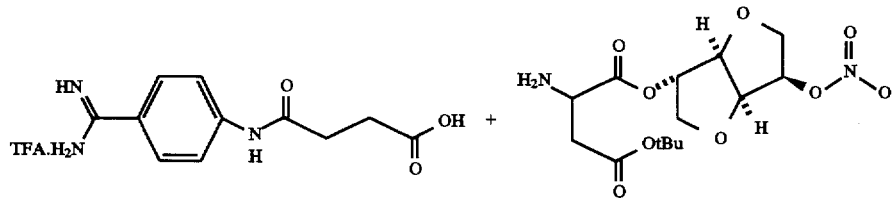
1. isobutylchloroformate/NMM
2. TFA
↓

-continued
SCHEME II

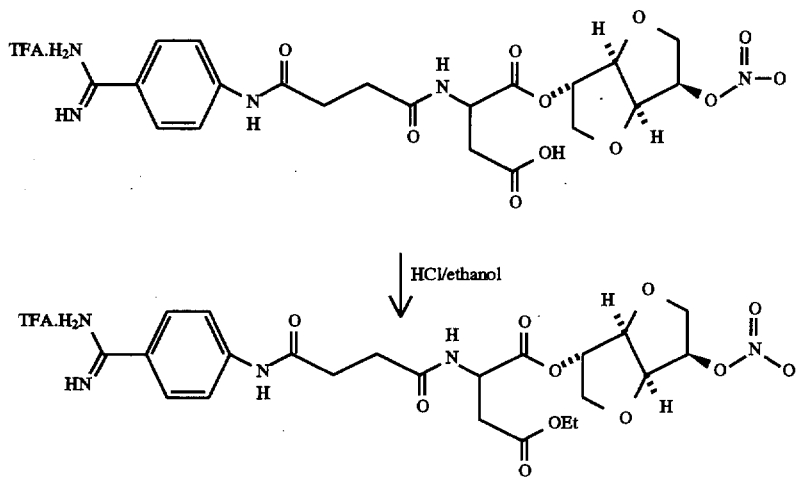

It will be obvious to one skilled in the art to make modifications in the choice of starting materials and process conditions to make all of the invention compounds disclosed herein.

The invention is illustrated by the following examples:

EXAMPLE 1

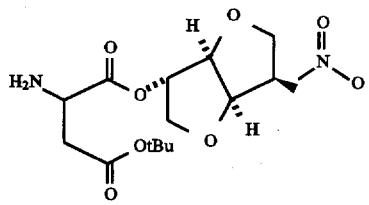

Fmoc-Asp(OtBu)—OH (5.0 g; 10 mmoles), isosorbide-5-mononitrate (2.0 g; 10 mmoles) and 4-dimethylaminopyridine (DMAP, 100 mg) were dissolved in dichloromethane (150 ml). To this solution, N,N'-dicyclohexylcarbodiimide (DCC, 2.3 g; 12 mmoles) was added with stirring. The mixture was stirred over weekend at room temperature. A small sample was taken for mass spectrometry, which indicated the presence of the desired intermediate (FAB-MS: (M+Li)$^+$=591). The solid urea was removed by filtration and the filtrate was treated with diethylamine (DEA, 40 ml) for one hour. The solvent was removed on a rotavapor and the residue was used without any further purification. FAB-MS: (M+Li)$^+$=369.

EXAMPLE 2

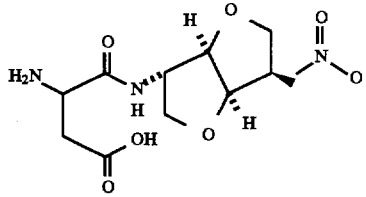

The title compound is prepared from Fmoc-Asp(OtBu)—OH and 2-amino-1,4:3,6-dianhydrosorbitol-5-nitrate according to procedure described in Example 1.

EXAMPLE 3

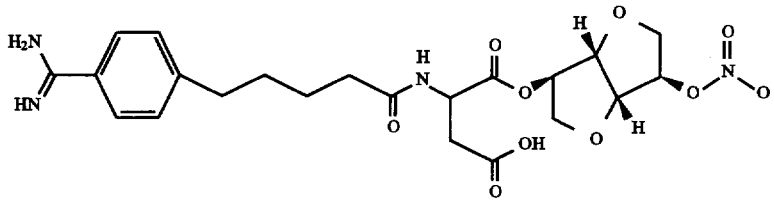

4-amidinophenylpentanoic acid.HCl (2.6 g; 10 mmoles), disuccinimidyl carbonate (DSC, 2.5 g; 10 mmoles) and 4-dimethylaminopyridine (0.5 g) were stirred in dimethylformamide/pyridine (3:1; 200 ml) overnight. To this mixture, Asp(OtBu)-isosorbide-5-mononitrate ester (EXAMPLE 1) was added slowly. The reaction mixture was stirred at room temperature for another day and filtered. A small sample was taken from the filtrate for mass spectrometry, which indicated the presence of the desired intermediate (FAB-MS: (M+H)$^+$=565). The filtrate was taken down to dryness and the residue was treated with trifluoroacetic acid (TFA, 100 ml) for one hour. The acid was removed under reduced pressure on rotavapor and the oily residue was purified by reverse phase preparative HPLC on a Deltapak C$_{18}$ column using a linear gradient of 5% to 50% acetonitrile/water/0.05% trifluoroacetic acid. The product was lyophilized to give 450 mg of white solid. FAB-MS: (M+H)⁺=508.9. $^1$H-NMR (DMSO-$d_6$) 1.4–1.6 (m, 4H, —CH$_2$—CH$_2$—), 2.15 (t, 2H, CH$_2$-phenyl), 4.35 and 5.1 (d, 2H, isosorbide), 4.5 (q, 1H, α-CH), 4.92 and 5.5 (t, 2H, isosorbide), 7.4 and 7.75 (dd, 4H, phenyl), 8.34 (m, 1H, NH), 9.05 and 9.2 (s, 2H, amidine)

EXAMPLE 4

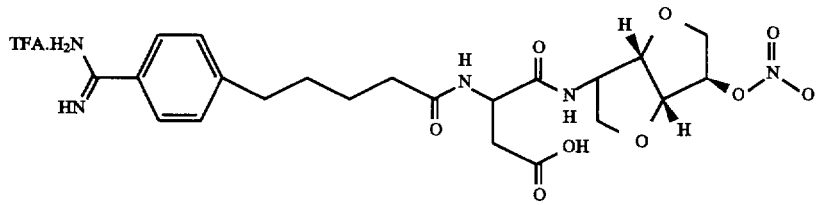

The title compound is prepared from 4-amidinophenylpentanoic acid.HCl and the title product of EXAMPLE 2 according to procedure described in Example 3.

EXAMPLE 5

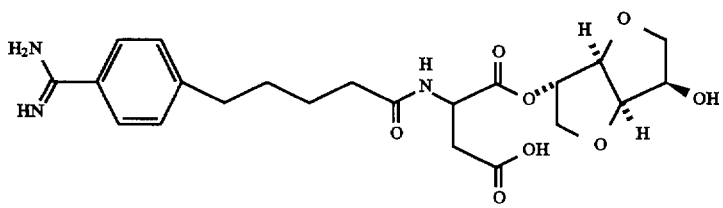

EXAMPLE 3 (100 mg) was dissolved in a phosphate buffered saline solution (pH 7.4; 10 ml) containing 10 mM cysteine and the mixture was stirred at room temperature over weekend. The reaction progress was monitored by analytical HPLC. The mixture was then purified by preparative reverse phase HPLC on a Deltapak C$_{18}$ column using a linear gradient of 5% to 50% acetonitrile/water/0.05% trifluoroacetic acid. The product was lyophilized to give 5 mg of white solid. FAB-MS: (M+H)⁺=464.4.

EXAMPLE 6

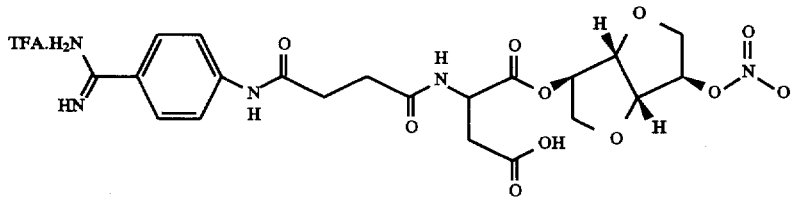

4-[[4-amidinophenyl]-amino]-4-oxobutanoic acid.TFA (3.5 g; 10 mmoles) was added to dry dimethylformamide (100 ml) followed by N-methylmorpholine (NMM, 1 g; 10 mmoles) and isobutylchloroformate (1.37 g; 10 mmoles) at room temperature. To this mixture, Asp(OtBu)-isosorbide-5-mononitrate ester (EXAMPLE 1; ~10 mmoles) was added followed by N-methylmorpholine (1 g; 10 mmoles). The reaction mixture was stirred at room temperature for 2 hours and filtered. The filtrate was taken down to dryness and the residue was treated with trifluoroacetic acid (TFA, 50 ml) for one hour. The acid was removed under reduced pressure on rotavapor and the oily residue was purified by preparative reverse phase HPLC on a Deltapak C$_{18}$ column using a linear gradient of 5% to 50% acetonitrile/water/0.05% trifluoroacetic acid. The product was lyophilized to give 700 mg of white solid. FAB-MS: (M+H)⁺=524.4. $^1$H-NMR (DMSO-$d_6$) 4.35 and 5.05 (d, 2H, isosorbide), 4.5 (q, 1H, α-CH), 4.92 and 5.5 (m, 2H, isosorbide), 7.75 (s, 4H, phenyl), 8.44 (m, 1H, NH), 8.85 and 9.15 (s, 2H, amidine)

EXAMPLE 7

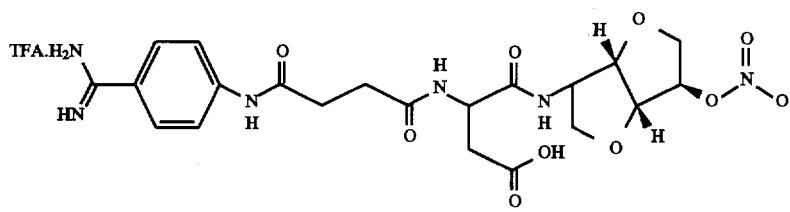

The title compound is prepared from 4-[[4-amidinophenyl]-amino]-4-oxobutanoic acid.TFA and the title product of EXAMPLE 2 according to procedure described in Example 6.

EXAMPLE 8

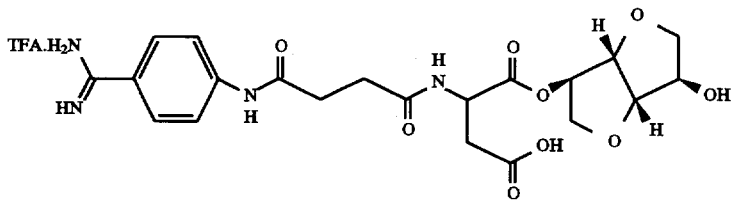

EXAMPLE 6 (100 mg) was dissolved in a dilute sodium bicarbonate solution (pH 7.4; 5 ml) containing 10 mM cysteine and the mixture was stirred at room temperature overnight. The reaction progress was monitored by analytical HPLC. The mixture was then purified by preparative reverse phase HPLC on a Deltapak $C_{18}$ column using a linear gradient of 5% to 50% acetonitril/water/0.05% trifluoroacetic acid. The product was lyophilized to give 40 mg of white solid. FAB-MS: $(M+H)^+=479.4$

EXAMPLE 9

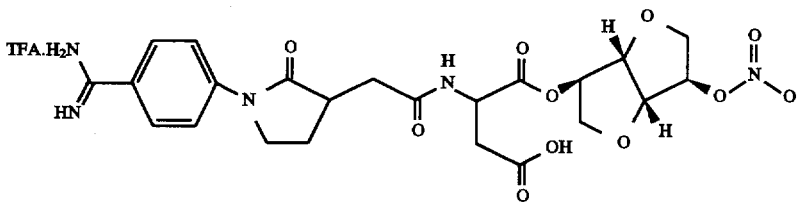

The title compound is prepared from α-[[1-[4-(aminoiminomethyl)phenyl]-2-oxo-pyrrolidin-3-yl]acetic acid and the title product of EXAMPLE 1 according to procedure described in EXAMPLE 3.

EXAMPLE 10

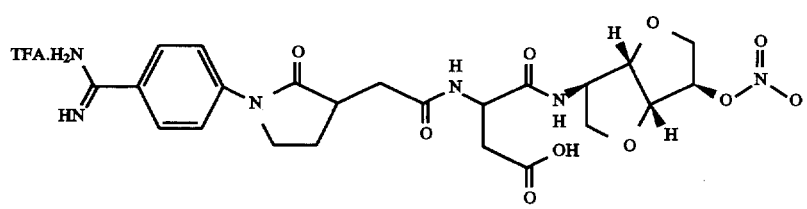

The title compound is prepared from α-[1-[4-(aminoiminomethyl)phenyl]-2-oxo-pyrrolidin-3-yl]acetic acid and the title product of EXAMPLE 2 according to procedure described in EXAMPLE 3.

EXAMPLE 11

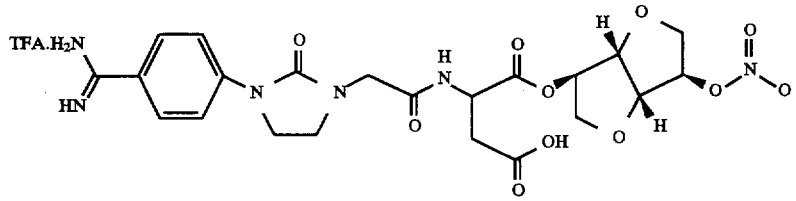

The title compound is prepared from α-[1-[4-(aminoiminomethyl)phenyl]-2-imidazolinon-3-yl]acetic acid and the title product of EXAMPLE 1 according to procedure described in EXAMPLE 3.

EXAMPLE 12

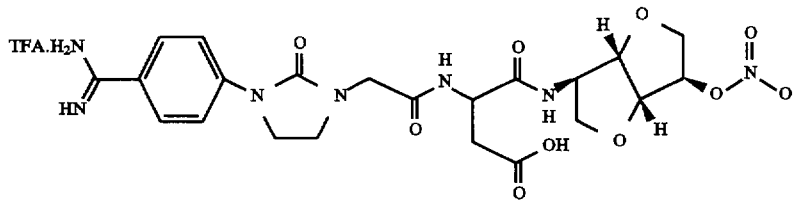

The title compound is prepared from α-[1-[4-(aminoiminomethyl)phenyl]-2-imidazolinon-3-yl]acetic acid and the title product of EXAMPLE 2 according to procedure described in EXAMPLE 3.

EXAMPLE 13

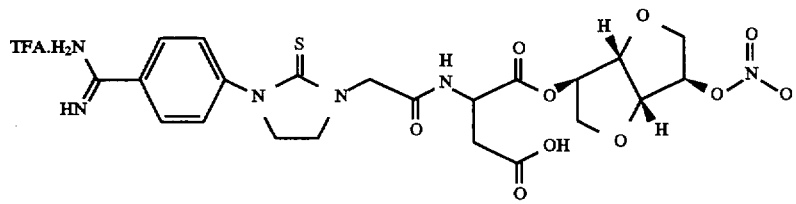

The title compound is prepared from α-[1-[4-(aminoiminomethyl)phenyl]-2-mercapto-imidazolidin-3-yl] acetic acid and the title product of EXAMPLE 1 according to procedure described in EXAMPLE 3.

EXAMPLE 14

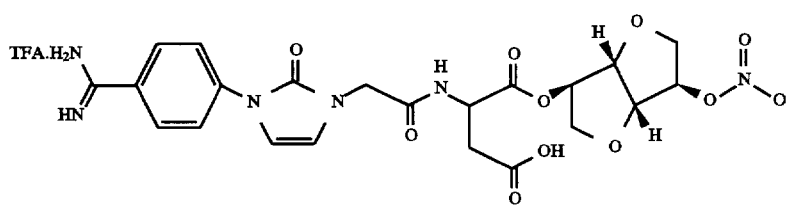

The title compound is prepared from α-[1-[4-(aminoiminomethyl)phenyl]-2(3H)-oxo-1H-imidazol-3-yl] acetic acid and the title product of EXAMPLE 1 according to procedure described in EXAMPLE 3.

EXAMPLE 15

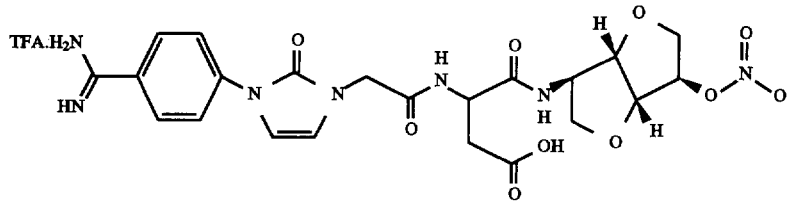

The title compound is prepared from α-[1-[4-(aminoiminomethyl)phenyl]-2(3H)-oxo-1H-imidazol-3-yl] acetic acid and the title product of EXAMPLE 2 according to procedure described in Example 3.

EXAMPLE 16

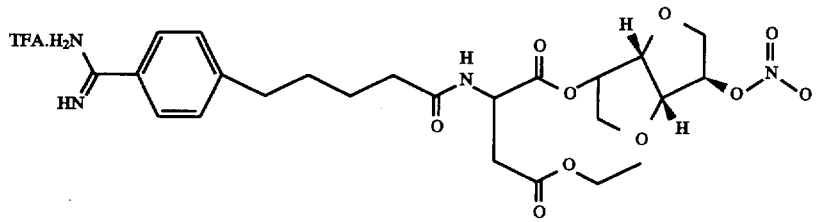

The product of EXAMPLE 3 (25 mg) was treated with HCl(gas) saturated ethanol solution (5 ml). The mixture was taken down to dryness under reduced pressure and the residue was purified by reverse phase HPLC on a Deltapak $C_{18}$ column using a linear gradient of 5% to 50% acetonitrile/water/0.05% trifluoroacetic acid. The product was lyophilized to give 20 mg of white solid. FAB-MS: $(M+H)^+$=536.9. $^1$H-NMR (DMSO-$d_6$) 1.18 (t, 3H, CH$_3$), 1.4–1.6 (m, 4H, —CH$_2$—CH$_2$—), 2.1 (t, 2H, CH$_2$-phenyl), 4.05 (m, 2H, —OCH$_2$—), 4.35 and 5.1 (d, 2H, isosorbide), 4.5 (q, 1H, α-CH), 4.95 and 5.5 (t, 2H, isosorbide), 7.4 and 7.75 (dd, 4H, phenyl), 8.38 (m, 1H, NH), 8.95 and 9.1 (s, 2H, amidine)

EXAMPLE 17

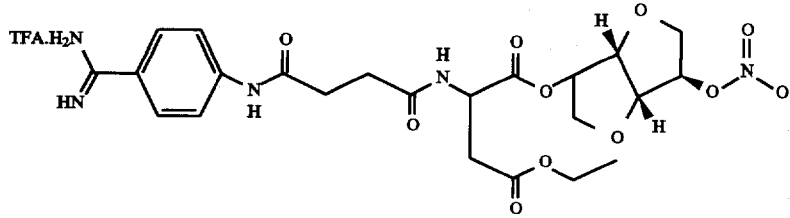

The product of EXAMPLE 6 (25 mg) was treated with HCl(gas) saturated ethanol solution by the method of EXAMPLE 16 to generate the title compound as a white solid (20 mg). FAB-MS: $(M+H)^+$=552.5. $^1$H-NMR (DMSO-$d_6$) 1.18 (t, 3H, CH$_3$), 4.05 (m, 2H, —OCH$_2$—), 4.35 and 5.05 (d, 2H, isosorbide), 4.5 (q, 1H, α-CH), 4.92 and 5.5 (m, 2H, isosorbide), 7.75 (s, 4H, phenyl), 8.44 (m, 1H, NH), 8.75 and 9.15 (s, 2H, amidine)

EXAMPLE 18

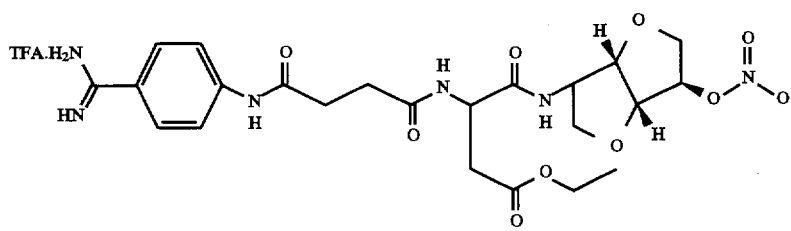

The product of EXAMPLE 7 is treated with HCl(gas) saturated ethanol solution by the method of EXAMPLE 16 to generate the title compound.

EXAMPLE 19

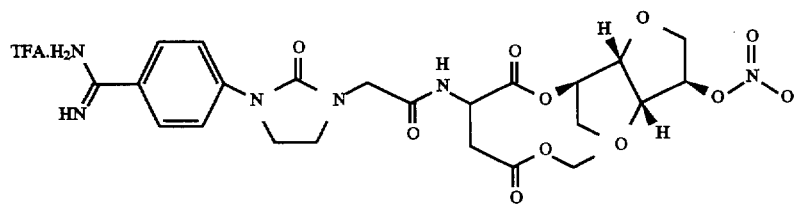

The product of EXAMPLE 11 is treated with HCl(gas) saturated ethanol solution by the method of EXAMPLE 16 to generate the title compound.

EXAMPLE 20

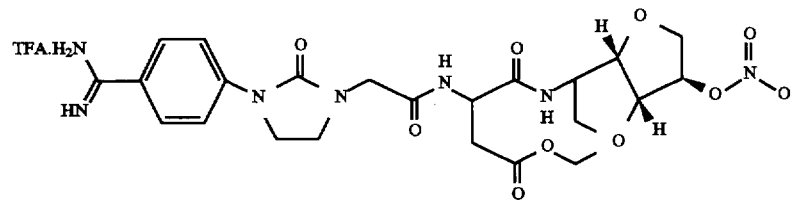

The product of EXAMPLE 12 is treated with HCl(gas) saturated ethanol solution by the method of EXAMPLE 16 to generate the title compound.

EXAMPLE 21

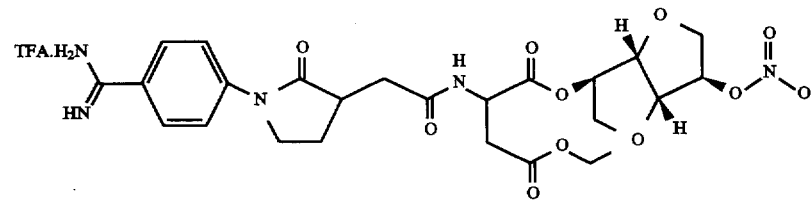

The product of EXAMPLE 9 is treated with HCl(gas) saturated ethanol solution by the method of EXAMPLE 16 to generate the title compound.

EXAMPLE 22

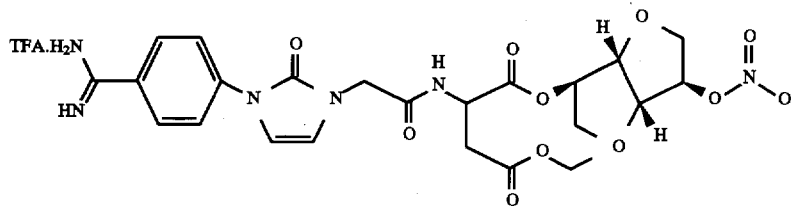

The product of EXAMPLE 14 is treated with HCl(gas) saturated ethanol solution by the method of EXAMPLE 16 to generate the title compound.

BIOLOGY

The compounds of the above invention were tested in the in vitro human platelet aggregation assay in platelet rich plasma (PRP) and in the competitive solid phase binding assay against purified human fibrinogen and vitronectin receptors.

In-Vitro Human Platelet Aggregation in PRP:

Healthy male or female donors who have not taken any antiplatelet drugs for at least two weeks were fasted for 8 hours prior to drawing blood; then 30 mL whole blood was collected using a butterfly needle and 30 cc plastic syringe with 3 mL of 0.129M buffered sodium citrate (3.8%). The syringe was rotated carefully as blood was drawn to mix the citrate. Platelet-rich plasma (PRP) was prepared by centrifugation at 250× g for 12 minutes at room temperature, allowing the centrifuge to coast to a stop without braking. The PRP was removed from the blood with a plastic pipette and placed in a plastic capped, 50 mL Corning conical sterile centrifuge tube which was held at room temperature. Platelet-poor plasma (PPP) was prepared by centrifuging the remaining blood at 2000× g for 15 minutes at room temperature allowing the centrifuge to coast to a stop without braking. The PRP was adjusted with PPP to a count of 2–3×10$^8$ platelets per mL. 450 μL of the PRP preparation and 50 μL of the compound to be tested or saline were preincubated for 1 minute at 37° C. in a Payton aggregometer (Payton Scientific, Inc., Buffalo, N.Y.). 50 μL of adenosine 5'-diphosphate (ADP) (200 mM) was added to the cuvettes and the aggregation was monitored for 1 minute. All compounds are tested in duplicate. Results are calculated as follows: Percent of control=[(maximal OD minus initial OD of compound) divided by (maximal OD minus initial OD of control saline)]×100. The % inhibition=100-(percent of control). The compounds tested and their activity results at median inhibitory concentration (IC$_{50}$) were as recorded in Table 1.

TABLE 1

Inhibition of ADP-Induced Platelet Aggregation in Human PRP

| Compound | IC$_{50}$ [μM] |
|---|---|
| Example 3 | 2.0 |
| Example 5 | 2.0 |
| Example 6 | 0.4 |
| Example 8 | 0.3 |

Solid Phase Receptor Assays

These assays were essentially the same as previously reported. The purified human vitronectin receptor(α$_v$β$_3$) or purified human fibrinogen receptor(IIb$^β$3) were diluted from stock solutions to 1.0 μg/mL in Tris-buffered saline containing 1.0 mM Ca$^{++}$, Mg$^{++}$, and Mn$^{++}$, pH 7.4 (TBS$^{+++}$). The diluted receptor was immediately transferred to Linbro microtiter plates at 100 μL/well (100 ng receptor/well). The plates were sealed and incubated overnight at 4° C. to allow the receptor to bind to the wells. All remaining steps were at room temperature. The assay plates are emptied and 200 μL of 1% radioimmunoassay grade bovine serum albumin in TBS$^{+++}$ (TBS$^{+++}$/BSA) were added to block exposed plastic surfaces. Following a 2 hour incubation, the assay plates were washed with TBS$^{+++}$ using a 96 well plate washer. Logarithmic serial dilution of the test compound and controls were made starting at a stock concentration of 2 mM and using 2 nM biotinylated vitronectin in TBS$^{+++}$/BSA as the diluent. This premixing of labeled ligand with test (or control) ligand, and subsequent transfer of 50 μL aliquots to the assay plate was carried out with a CETUS Propette robot; the final concentration of the labeled ligand was 1 nM and the highest concentration of test compound was 1.0× 10$^{-4}$M. The competition occurred for two hours after which all wells were washed with a plate washer as before. Affinity purified horseradish peroxidase labeled goat anti-biotin antibody was diluted 1:3000 in TBS$^{+++}$/BSA and 125 μL were added to each well. After 30 minutes, the plates were washed and incubated with o-phenylendiamine/H$_2$O$_2$ substrate in 100 mM/L Citrate buffer, pH 5.0. The plate was read with a microtiter plate reader at a wavelength of 450 nm and when the maximum-binding control wells reached an absorbance of about 1.0, the final A$_{450}$ were recorded for analysis. The data were analyzed using a macro written for use with the EXCEL™ spreadsheet program. The mean, standard deviation, and % coefficient variation were determined for duplicate concentrations. The mean A$_{450}$ values were normalized to the mean of four maximum-binding controls (no competitor added). The normalized values were subjected to a four parameter curve fit algorithm, plotted on a semi-log scale, and the computed IC$_{50}$ and corresponding correlation coefficient was reported. GRGDSP, a peptide fragment of fibrinogen, was included on each plate as a positive control.

TABLE 2

Competitive Binding Assays to Purified Human Fibrinogen and Vitronectin Receptors

| | IC$_{50}$ [nM] | |
|---|---|---|
| Compound | Fibrinogen receptor | Vitronetin receptor |
| Example 3 | 3.11 | >100,000 |
| Example 5 | 1.28 | >100,000 |
| Example 6 | 0.25 | >100,000 |
| Example 8 | 0.71 | >100,000 |

From the foregoing description, one skilled in the art can easily ascertain the essential characteristics of this invention, and without departing from the spirit and scope thereof, can make various changes and modifications of the invention to adapt it to various usages and conditions.

What is claimed:
1. A compound having the formula:

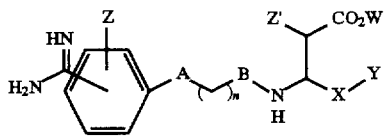
(I)

or a pharmaceutically acceptable salt thereof, wherein;

A is independently selected from the group consisting of

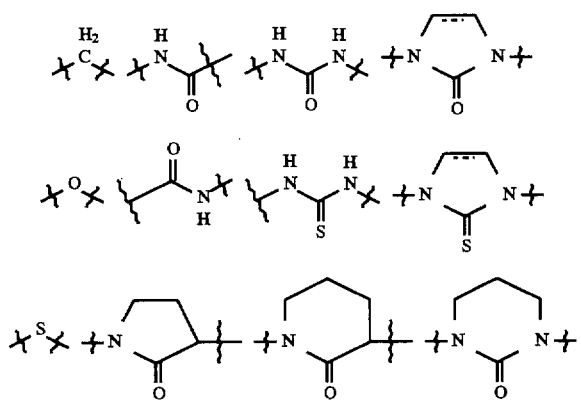

wherein the dotted line indicates a single or a double bond and

B is selected from a group consisting of carbonyl or iminocarbonyl group;

W is selected from the group consisting of hydrogen, lower alkyl radicals, lower alkenyl radicals, lower alkynyl radicals, alicyclic hydrocarbon radicals and aromatic hydrocarbon radicals, wherein all of said radicals are optionally substituted with hydroxyl, lower alkyl, lower alkoxy, halogen, nitro, amino, acyloxy, phenyl and naphthyl which may be optionally substituted with halogen, nitro, lower alkoxy, and lower alkyl;

Z, Z' are independently selected from the group consisting of hydrogen, halogen, cyano, sulfonyl, hydroxy, lower alkoxy, and lower alkyl radicals;

X is a carbonyl, alicyclic or heterocyclic radicals;

Y is one of the following;

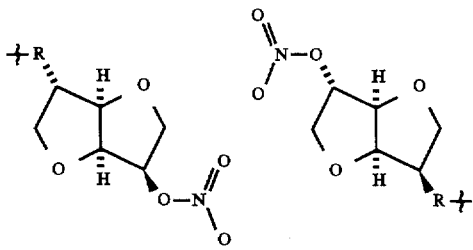

wherein R is an oxygen or an imino group;

n is an integer 1 to about 4.

2. The compound as recited in claim 1 wherein;

A is selected from the group consisting of

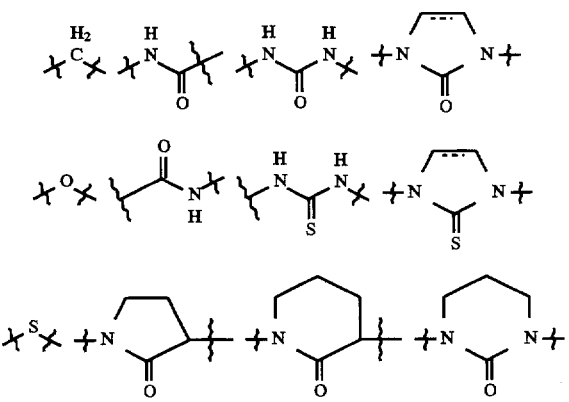

wherein the dotted line indicates a single or a double bond

B is selected from a group consisting of carbonyl or iminocarbonyl group;

W is selected from the group consisting of hydrogen, lower alkyl radicals of 1 to about 6 carbon atoms, lower alkenyl radicals of 2 to about 6 carbon atoms, alicyclic hydrocarbon radicals of 3 to about 6 carbon atoms, and aromatic hydrocarbon radicals of 6 to about 12 carbon atoms, wherein all of said radicals are optionally substituted with hydroxyl, lower alkoxy, lower alkyl, halogen, nitro, amino, and acyloxy;

Z, Z' are independently selected from the group consisting of hydrogen, halogen, cyano, sulfonyl, hydroxy, lower alkyl and lower alkoxy radicals;

X is a carbonyl, alicyclic or heterocyclic radicals;

Y is one of the following;

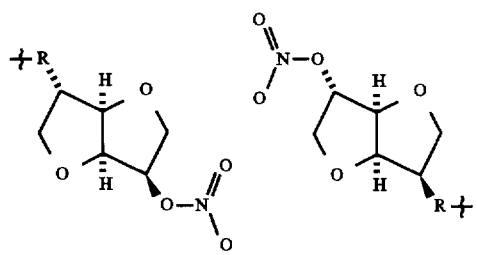

wherein R is an oxygen or an imino group; and n is an integer 1 to about 4.

3. The compound as recited in claim 2 wherein;

A is selected from the group consisting of

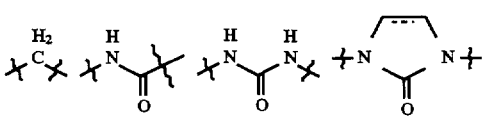

-continued

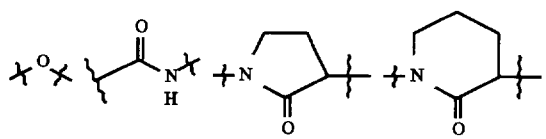

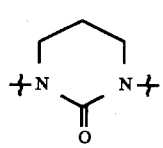

wherein the dotted line indicates a single or a double bond

B is selected from a group consisting of carbonyl or iminocarbonyl radicals;

W is selected from the group consisting of hydrogen, lower alkyl radicals of 1 to about 6 carbon atoms, alicyclic hydrocarbon radicals of 3 to about 6 carbon atoms, and aromatic hydrocarbon radicals of 6 to about 12 carbon atoms, wherein all of said radicals are optionally substituted with hydroxyl, lower alkoxy, lower alkyl, halogen, nitro, amino, and acyloxy;

Z, Z' are independently selected from the group consisting of hydrogen, halogen, alkoxy, and lower alkyl radicals;

X is a carbonyl or alicyclic radicals;

Y is one of the following;

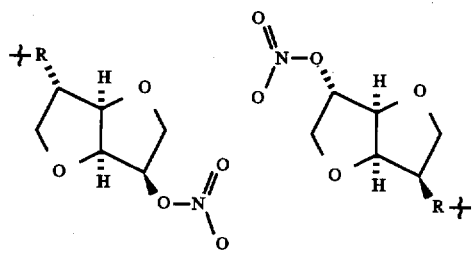

wherein R is an oxygen or an imino group; and n is an integer 1 to about 3.

4. The compound as recited in claim 3 wherein A is

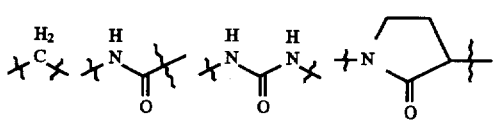

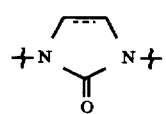

wherein the dotted line indicates a single or a double bond

B is selected from a group consisting of carbonyl or iminocarbonyl radicals;

W is selected from the group consisting of hydrogen, methyl, ethyl, propyl, cyclohexyl radicals;

Z, Z' are independently selected from the group consisting of hydrogen and hydroxy radicals;

X is a carbonyl or alicyclic radicals;

Y is one of the following;

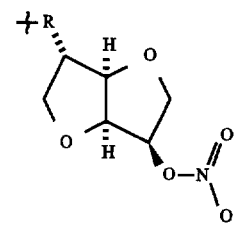

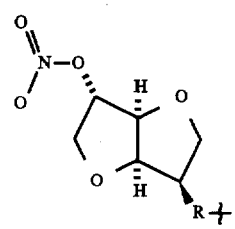

wherein R is an oxygen or an imino group; and n is an integer 1 to 3.

5. The compound as recited in claim 4 wherein A is

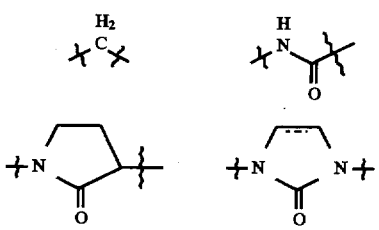

wherein the dotted line indicates a single or a double bond and B is a carbonyl group;

W is selected from the group consisting of hydrogen, ethyl and cyclohexyl radicals;

Z, Z' are hydrogen;

X is a carbonyl radical;

Y is one of the following:

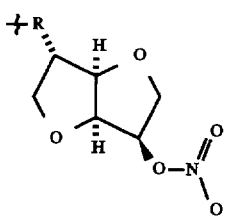

-continued

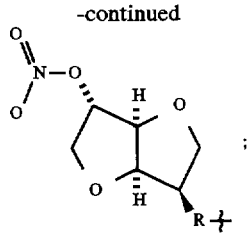

wherein R is an oxygen; and n is an integer 1 to 2.

6. A pharmaceutical composition comprising a compound of claim 1,2,3,4, or 5 and together with at least one non-toxic pharmaceutical acceptable carrier.

7. A method of treating a mammal to inhibit platelet aggregation and to promote vasodilation in a mammal in need of such treatment comprising administering a therapeutically effective amount of at least one compound of claim 1,2,3,4, or 5.

* * * * *

UNITED STATES PATENT AND TRADEMARK OFFICE
CERTIFICATE OF CORRECTION

PATENT NO. : 5,674,894

DATED : October 7, 1997

INVENTOR(S) : Currie et al.

It is certified that error appears in the above-identified patent and that said Letters Patent is hereby corrected as shown below:

Column 1, line 60, delete "Applications" and substitute therefor --Application--.

Column 1, line 64, delete "Applications" and substitute therefor --Application--.

Column 2, line 15, delete "Applications" and substitute therefor --Application--.

Column 2, line 47, delete "*Pharmacoloaical*" and substitute therefor --*Pharmacological*--.

Column 2, line 50, delete "*Pharmacolgy*" and substitute therefor --*Pharmacology*--.

UNITED STATES PATENT AND TRADEMARK OFFICE
CERTIFICATE OF CORRECTION

PATENT NO. : 5,674,894

DATED : October 7, 1997

INVENTOR(S) : Currie et al.

It is certified that error appears in the above-identified patent and that said Letters Patent is hereby corrected as shown below:

Column 5, line 40, delete the following formula:

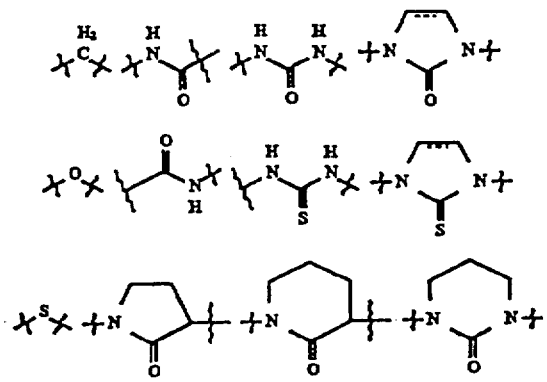

and substitute therefor --

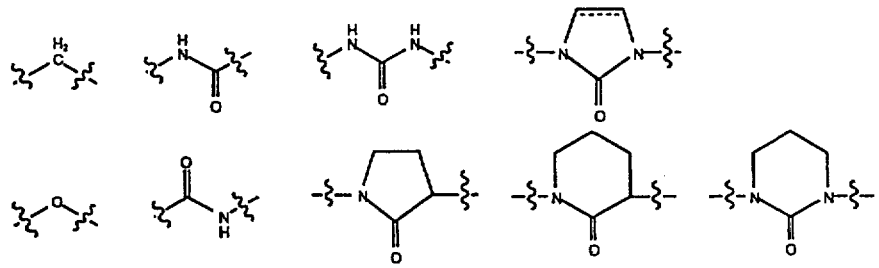

UNITED STATES PATENT AND TRADEMARK OFFICE
CERTIFICATE OF CORRECTION

PATENT NO. : 5,674,894

DATED : October 7, 1997

INVENTOR(S) : Currie et al.

It is certified that error appears in the above-identified patent and that said Letters Patent is hereby corrected as shown below:

Column 6, line 31, delete the following formula:

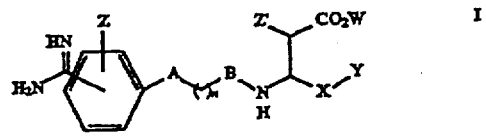

and substitute therefor --

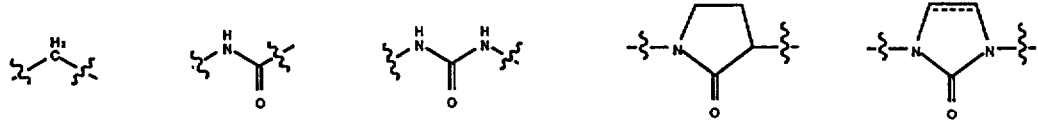

UNITED STATES PATENT AND TRADEMARK OFFICE
CERTIFICATE OF CORRECTION

PATENT NO. : 5,674,894
DATED : October 7, 1997
INVENTOR(S) : Currie et al.

It is certified that error appears in the above-identified patent and that said Letters Patent is hereby corrected as shown below:

Column 9, line 30, delete "a" and substitute therefor --an--.

Column 11, delete the following formula for HCl/ethanol:

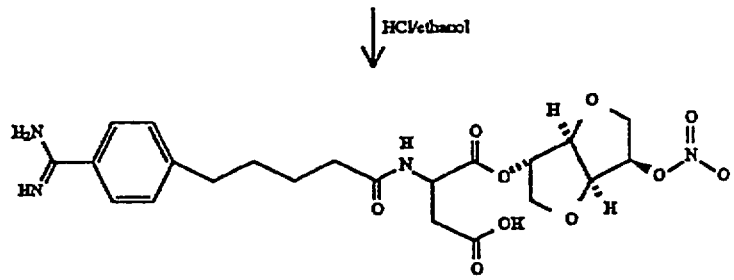

UNITED STATES PATENT AND TRADEMARK OFFICE
CERTIFICATE OF CORRECTION

PATENT NO. : 5,674,894
DATED : October 7, 1997
INVENTOR(S) : Currie et al.

It is certified that error appears in the above-identified patent and that said Letters Patent is hereby corrected as shown below:

and substitute therefor --

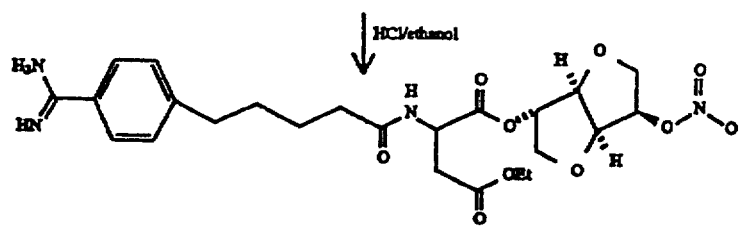

Signed and Sealed this

Twelfth Day of May, 1998

*Attest:*

*Attesting Officer*

BRUCE LEHMAN

*Commissioner of Patents and Trademarks*